(12) United States Patent
Hart et al.

(10) Patent No.: US 9,072,480 B2
(45) Date of Patent: Jul. 7, 2015

(54) UNIVERSAL LAPAROSCOPIC SUTURING DEVICE

(71) Applicant: University of South Florida, Tampa, FL (US)

(72) Inventors: Stuart Hart, Tampa, FL (US); Sinan Onal, Tampa, FL (US); Susana K. Lai-Yuen, Tampa, FL (US)

(73) Assignee: University of South Florida, Tampa, FL (US)

( * ) Notice: Subject to any disclaimer, the term of this patent is extended or adjusted under 35 U.S.C. 154(b) by 144 days.

(21) Appl. No.: 13/758,454

(22) Filed: Feb. 4, 2013

(65) Prior Publication Data

US 2013/0144315 A1 Jun. 6, 2013

Related U.S. Application Data

(63) Continuation of application No. PCT/US2011/046270, filed on Aug. 2, 2011.

(60) Provisional application No. 61/369,902, filed on Aug. 2, 2010.

(51) Int. Cl.
*A61B 17/04* (2006.01)
*A61B 17/12* (2006.01)
(Continued)

(52) U.S. Cl.
CPC ........... *A61B 1/3132* (2013.01); *A61B 1/00066* (2013.01); *A61B 17/0469* (2013.01); *A61B 17/0625* (2013.01); *A61B 2017/00367* (2013.01); *A61B 2017/0609* (2013.01)

(58) Field of Classification Search
CPC .................. A61B 17/0625; A61B 2017/0609; A61B 1/00066; A61B 1/3132; A61B 2017/00367; A61B 17/0469

USPC .................................................. 606/145, 144
See application file for complete search history.

(56) References Cited

U.S. PATENT DOCUMENTS 3,842,840 A * 10/1974 Schweizer .................... 606/145
4,312,337 A * 1/1982 Donohue ........................ 606/80
(Continued)

FOREIGN PATENT DOCUMENTS

| EP | 0687446 A2 | 12/1995 |
| WO | 9912482 A1 | 3/1999 |
| WO | 2009105487 A1 | 8/2009 |

OTHER PUBLICATIONS

International Search Report for Application No. PCT/US2011/046270, international filing date of Aug. 2, 2011, mailed on Mar. 15, 2012.

*Primary Examiner* — Tuan V Nguyen
*Assistant Examiner* — Chima Igboko
(74) *Attorney, Agent, or Firm* — Nicholas Pfeifer; Ronald E. Smith; Smith & Hopen, P.A.

(57) ABSTRACT

A laparoscopic suturing device includes a handle and a shaft mounted to the handle. A toggle knob is adapted to rotate the shaft about its longitudinal axis. A pair of opposed jaws, each having a hollow structure, open and close relative to one another. A needle carrier and a needle holder are respectively slideably disposed in a lumen of a first and a second jaw. A needle has first and second pointed ends and is adapted to be press fit into the lumen of the first jaw with the first pointed end exposed and alternatively into the lumen of the second jaw with the second pointed end exposed. A spring-loaded pusher advances and retracts the needle carrier when the toggle knob is in a first position and advances and retracts the needle holder when in a second position. The tool assists a surgeon in suturing tissue captured between the jaws.

7 Claims, 8 Drawing Sheets

(51) Int. Cl.
*A61B 1/313* (2006.01)
*A61B 1/00* (2006.01)
*A61B 17/062* (2006.01)
*A61B 17/00* (2006.01)
*A61B 17/06* (2006.01)

(56) References Cited

U.S. PATENT DOCUMENTS

| | | | | |
|---|---|---|---|---|
| 5,571,090 A | * | 11/1996 | Sherts | 606/144 |
| 5,632,746 A | * | 5/1997 | Middleman et al. | 606/78 |
| 5,645,552 A | * | 7/1997 | Sherts | 606/145 |
| 5,693,071 A | * | 12/1997 | Gorecki et al. | 606/222 |
| 5,713,908 A | * | 2/1998 | Jameel et al. | 606/148 |
| 5,730,747 A | * | 3/1998 | Ek et al. | 606/148 |
| 5,766,186 A | | 6/1998 | Faraz et al. | |
| 5,814,054 A | * | 9/1998 | Kortenbach et al. | 606/139 |
| 5,908,428 A | * | 6/1999 | Scirica et al. | 606/139 |
| 5,938,668 A | * | 8/1999 | Scirica et al. | 606/145 |
| 5,947,982 A | * | 9/1999 | Duran | 606/139 |
| 6,051,006 A | * | 4/2000 | Shluzas et al. | 606/148 |
| 6,056,771 A | * | 5/2000 | Proto | 606/222 |
| 7,615,059 B2 | * | 11/2009 | Watschke et al. | 606/144 |
| 2008/0140091 A1 | * | 6/2008 | DeDeyne et al. | 606/144 |
| 2009/0012538 A1 | * | 1/2009 | Saliman et al. | 606/145 |
| 2009/0177031 A1 | * | 7/2009 | Surti et al. | 600/106 |
| 2009/0312773 A1 | * | 12/2009 | Cabrera et al. | 606/144 |
| 2010/0004701 A1 | * | 1/2010 | Malandain et al. | 606/86 R |
| 2010/0057108 A1 | * | 3/2010 | Spivey et al. | 606/144 |
| 2010/0217282 A1 | * | 8/2010 | Cabrera et al. | 606/144 |
| 2010/0249497 A1 | * | 9/2010 | Peine et al. | 600/104 |
| 2011/0112555 A1 | * | 5/2011 | Overes et al. | 606/145 |
| 2011/0152891 A1 | * | 6/2011 | McLawhorn et al. | 606/145 |

* cited by examiner

UNIVERSAL LAPAROSCOPIC SUTURING DEVICE

BACKGROUND OF THE INVENTION

1. Field of the Invention

This invention relates, generally, to surgical instruments. More particularly, it relates to suturing and knot tying instruments for use during minimally invasive surgery.

2. Description of the Prior Art

Laparoscopic suturing is a challenging skill to master for surgeons performing laparoscopic surgery. It is often the rate-limiting step that prevents surgeons from performing more advanced surgical procedures in a minimally-invasive manner. Laparoscopic suturing is challenging for several reasons. First, the surgeon is operating in three dimensional space while viewing the procedure on a two dimensional screen. Second, grasping the small needle and placing the needle through tissue without wristed motion is very challenging since surgeons operate using elongated rigid shafts. Moreover, tying an appropriate knot after the suture is placed, and getting the knot secured to the appropriate tissue from a distance through small laparoscopic ports, is technically challenging.

Several conventional devices that assist surgeons in the performance of laparoscopic suturing are commercially available. Each of the known devices has various advantages and disadvantages, and most of these devices require the use of specific suture exclusively designed for the device. Since the suture for each of these devices is limited, the surgeon's choice of suture material is also limited. These specific sutures are also very expensive and reduce flexibility of suture available to the surgeon. Prior art sutures are also constructed with small needles attached to the end of the suture. The small needle can break during laparoscopic suturing and the small needle also limits the size of tissue that can be sutured.

Accordingly, there is a need for a suture assist device that works with any type of suture.

There is also a need for a more robust needle that is less subject to breakage than the needles heretofore known.

However, in view of the art considered as a whole at the time the present invention was made, it was not obvious to those of ordinary skill in the art how the needed improvements could be provided.

SUMMARY OF THE INVENTION

The long-standing but heretofore unfulfilled need for a laparoscopic suture assist device is now met by a new, useful, and non-obvious invention.

The novel laparoscopic suture assist device opens widely to suture large areas of tissue. It includes a preformed needle that drives any generic suture through the tissue. The device also enables suture to be placed as a single stitch, or as a running stitch. This increases flexibility for the surgeon and decreases operative expense. The device can be used to suture multiple times throughout the surgical procedure. The device also has a unique design that allows it to open wider than the diameter of the shaft of the instrument, to maximize the area of laparoscopic suturing available to the surgeon.

More particularly, the novel laparoscopic suturing device includes a handle and an elongate shaft rotatably mounted to the handle. A manually controlled toggle knob is secured to the elongate shaft so that manual rotation of the toggle knob rotates the elongate shaft about its longitudinal axis.

A pair of opposed jaws, each having a hollow structure, open and close relative to one another. The opposing jaws are biased relative to one another so that they are separated widely from one another when in repose. A surgeon manually advances a sheath that slideably ensleeves the shaft to close the jaws and retracts the sheath to allow them to open under their inherent bias.

A needle holder is slideably disposed in a lumen of a first jaw and a needle carrier is slideably disposed in a lumen of a second jaw. A truncate needle has a first pointed end and a second pointed end and is adapted to be press fit into the lumen of the first jaw with the first pointed end exposed and into the lumen of the second jaw with the second pointed end exposed.

A spring-loaded pusher is cooperatively positioned relative to the handle and is adapted to advance and retract the needle carrier when the toggle knob is in a first position and is adapted to advance and retract the needle holder when the toggle knob is in a second position. The tool assists a surgeon in suturing tissue captured between the jaws.

An important object of the invention is to provide a laparoscopic assist device that can be used with any type of suture.

Another important object is to provide such a device having a robust needle.

Another object is to enable the suturing of large areas of tissue.

Yet another object is to enable a suture to be placed as a single stitch or as a running stitch.

Still another object is to provide more options to laparoscopic surgeons and to reduce the expense of operations by providing instruments with improved maneuverability, efficiency and functionality.

These and other important objects, advantages, and features of the invention will become clear as this description proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

Figures 1A, 1B, 1C:
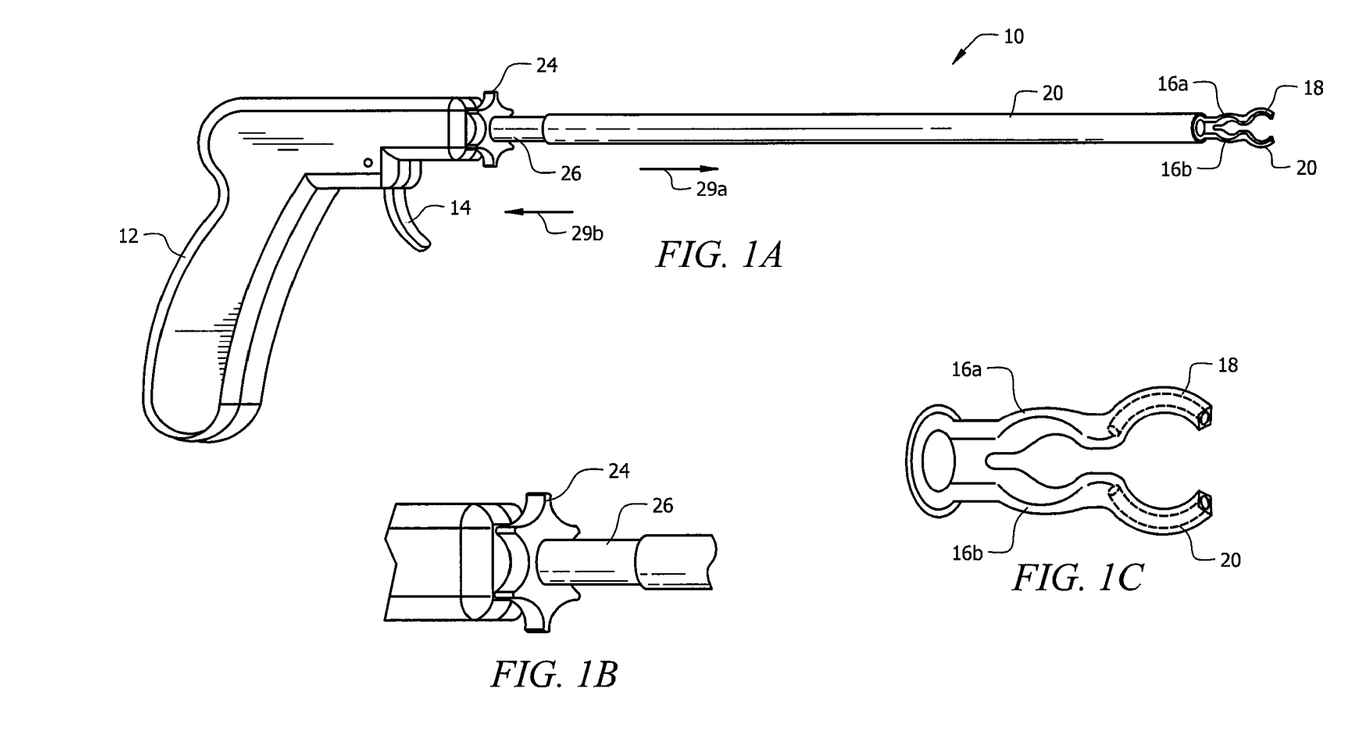
FIG. 1A is a perspective view of a first embodiment.
FIG. 1B is an enlarged perspective view of the toggle knob of the first embodiment.
FIG. 1C is an enlarged perspective view of the opposed arms of the first embodiment

FIG. 1A depicts an illustrative embodiment of the novel laparoscopic suture assist device which is denoted as a whole by the reference numeral 10.

Device 10 is an eleven and a half millimeter (11.5 mm) instrument that includes nine main parts. As depicted in FIGS. 1A, 1B, 1C, 2, and 3 those parts are handle 12, pusher 14, arms 16a, 16b, needle carrier 18, needle holder 20, needle 22, toggle knob 24, shaft 26 and sheath 28.

As will become clear as this disclosure continues, needle carrier 18 and needle holder 20 reverse roles as device 10 is used, i.e., needle 22 is carried by needle carrier 18, inserted into needle holder 20, and needle carrier is then withdrawn, leaving the needle in needle holder 20. Needle holder 20 then becomes the carrier as the needle is carried to needle carrier 18 and inserted thereinto with needle holder 20 then being withdrawn. This role reversal is repeated as needed throughout a suturing procedure.

Needle 22 is truncate in extent and is double pointed, i.e., its opposite ends are pointed. Accordingly, a first point is exposed to a suture when needle 22 is held by needle carrier 18 and a second point is exposed when needle 22 is held by needle holder 20.

Arms 16a, 16b are forced toward one another by sliding sheath 28 in a proximal to distal direction relative to shaft 26 as indicated by directional arrow 29a in FIG. 1A. Suture arms 16a, 16b are formed of a flexible, resilient material so that they return under their inherent bias to their depicted position of repose upon displacement of shaft 26 in the opposite direction, as indicated by directional arrow 29b in FIG. 1A.

Toggle knob 24 is rotatably mounted on shaft 26 so that said shaft rotates conjointly with rotation of toggle knob 24. Finger-receiving dishes are formed in the periphery of toggle knob 24 to facilitate manual gripping thereof.

FIGS. 2 through 6 provide a five step animation depicting how needle 22 is transferred from needle carrier 18 to needle holder 20. It should be understood that the same Figures can be interpreted as also disclosing the reverse procedure of transferring needle 22 from needle holder 20 to needle carrier 18.

Figure 2:
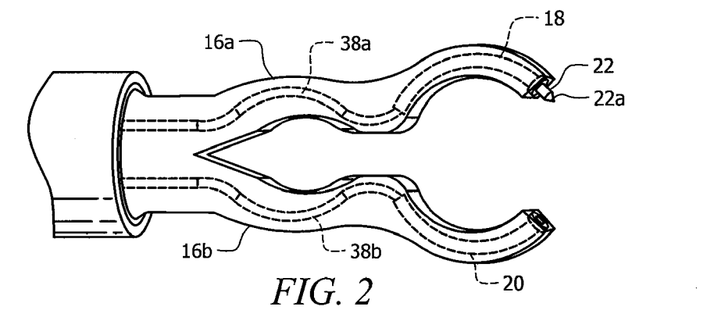
FIG. 2 is the first view of a five figure animation in perspective.

More particularly, FIG. 2 depicts needle carrier 18 and needle holder 20 in their respective fully retracted positions within the respective lumens of hollow arms 16a, 16b. Needle 22 is press fit into the distal free end of needle carrier 18. First pointed end 22a of needle 22 is exposed.

Figure 3:
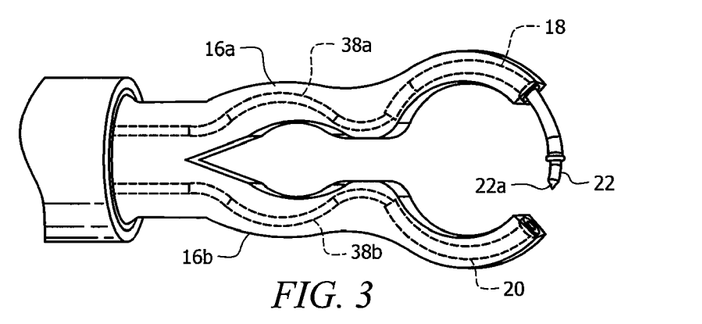
FIG. 3 is the second figure of said animation.

FIG. 3 depicts needle carrier 18 after it has been slidingly displaced in a proximal to distal direction, thereby carrying needle 22 to the position depicted. The displacement means is disclosed hereinafter.

Figure 4:
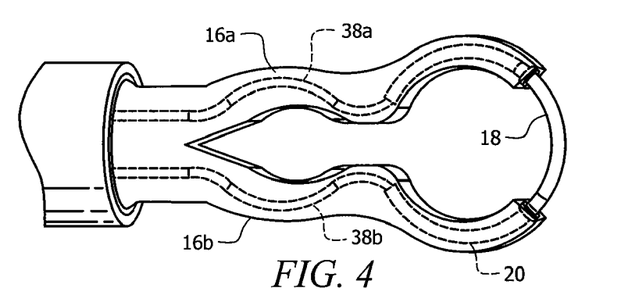
FIG. 4 is the third figure of said animation.

FIG. 4 depicts needle carrier 18 when fully extended. Pointed end 22a of needle 22 is now slideably received within the lumen of needle holder 20.

Figure 5:
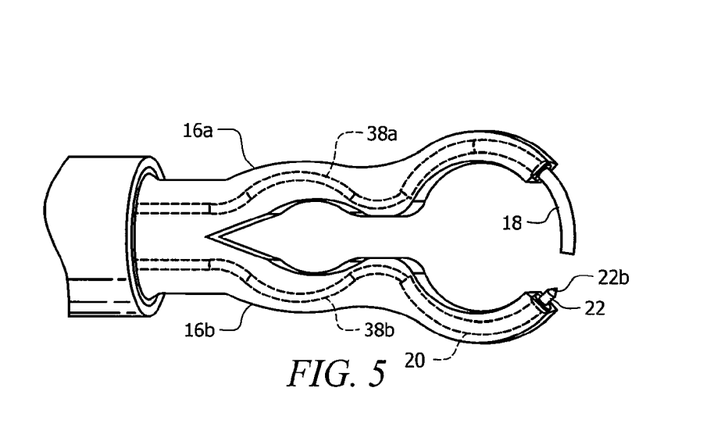
FIG. 5 is the fourth figure of said animation.

In FIG. 5, needle 22, with second pointed end 22b exposed, remains in the press fit grip of the lumen of needle holder 20 as needle carrier 18 is refracted by the displacement means disclosed hereinafter.

Figure 6:
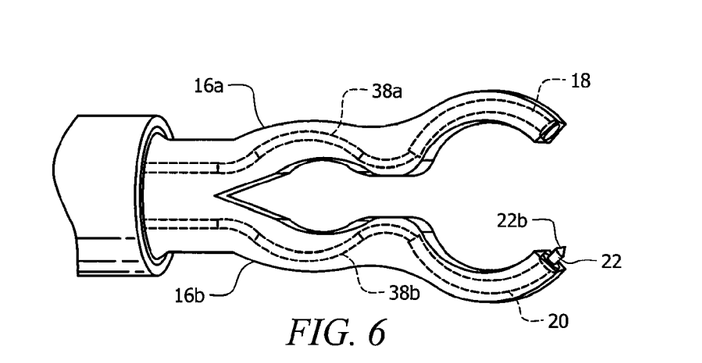
FIG. 6 is the sixth figure of said animation.

FIG. 6 depicts needle holder 18 fully retracted. Needle 22 remains in the grip of the lumen of needle holder 20.

Needle holder 20 is displaced by the same means as needle carrier 18. Accordingly, needle 22 can be returned to needle carrier 18, with point 22a exposed, by displacement of needle holder 20.

After needle 22 has been passed from needle carrier 18 to needle holder 20 as depicted in the five figure animation of FIGS. 2-6, the stitch is then pulled through the tissue. Needle 22 is then ready for the next maneuver.

Figure 10A:
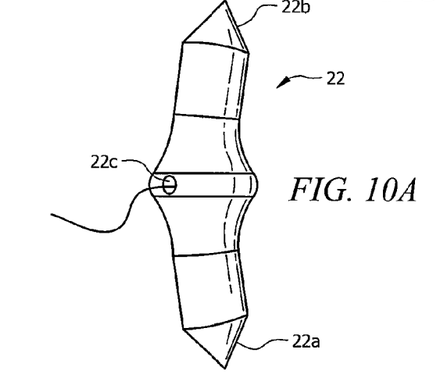
FIG. 10A is an elevational view of the novel double-pointed needle.

A suture is located in the middle of needle 22 and it causes needle 22 to passes through tissue easily. The suture is disposed within an opening in the middle of needle 22 as depicted in FIG. 10A. The suture may be anchored within the opening or threaded around a bar within the opening.

The structure depicted in FIGS. 7-11 enables a surgeon to retract and extend needle carrier 18 and needle holder 20 independently of one another to facilitate the tying of sutures.

Figure 7:
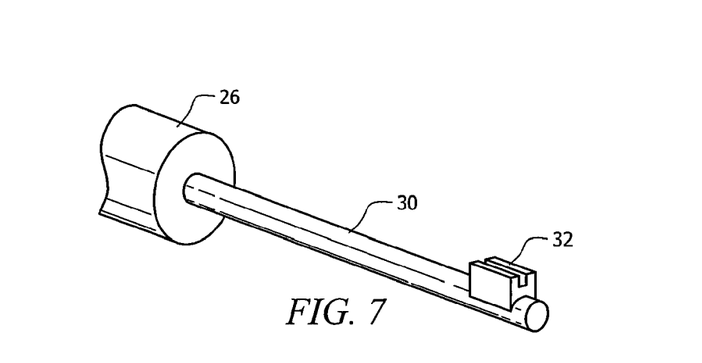
FIG. 7 is a perspective view of a first arm control plunger.
Figure 8:
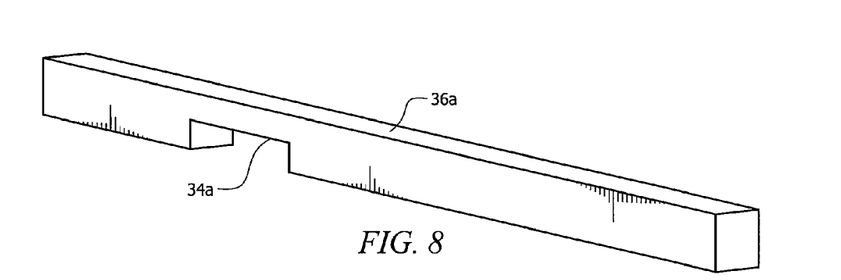
FIG. 8 is a perspective view of a plunger selector arm.
Figure 9A:
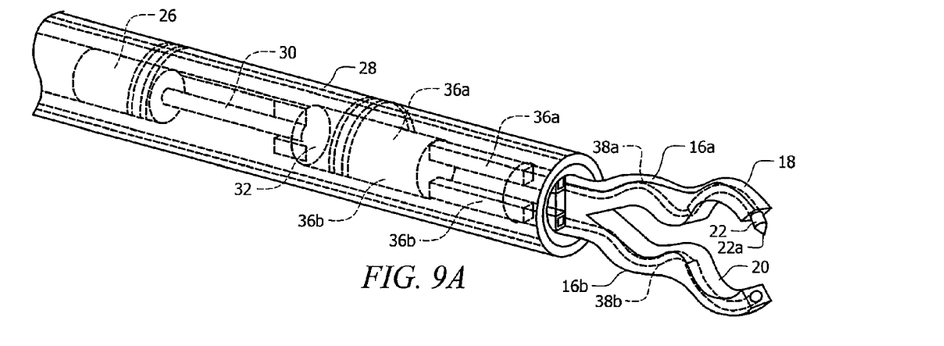
FIG. 9A is a perspective, transparent view of the plunger selector arm and arm control plunger assembly.
Figure 9B:
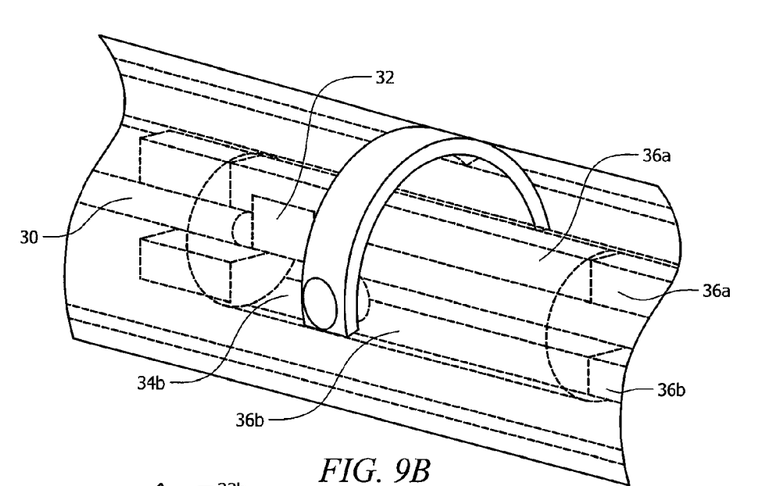
FIG. 9B is a perspective, enlarged view of the center of FIG. 9A.
Figure 11:
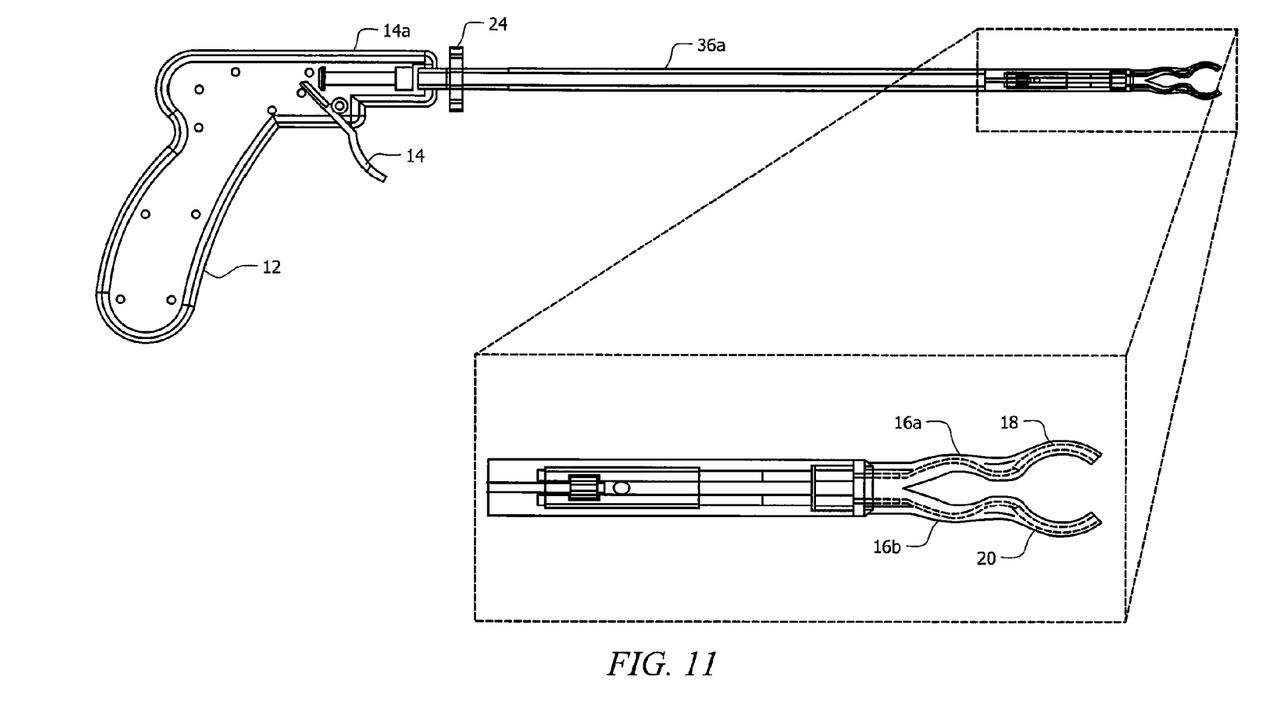
FIG. 11 is an exploded side elevational view of the novel structure.
Figure 12A:
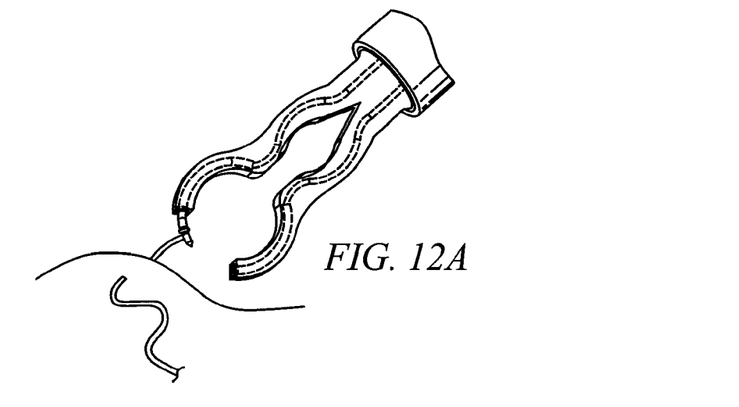
FIG. 12A is the first view of a six step animation depicting the steps of tying a square knot with the novel surgical tool.
Figure 12B:
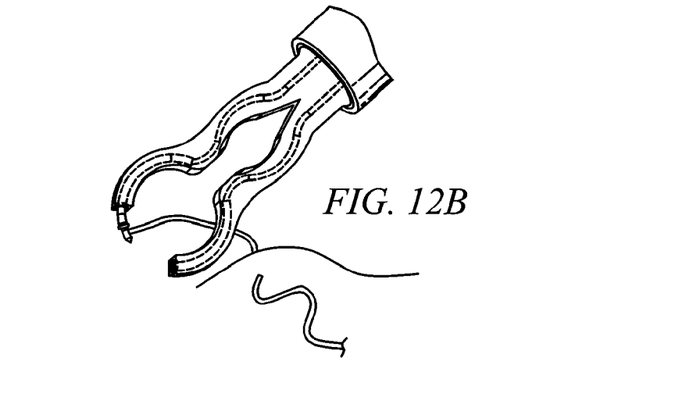
FIG. 12B is the second view of said six step animation.
Figure 12C:
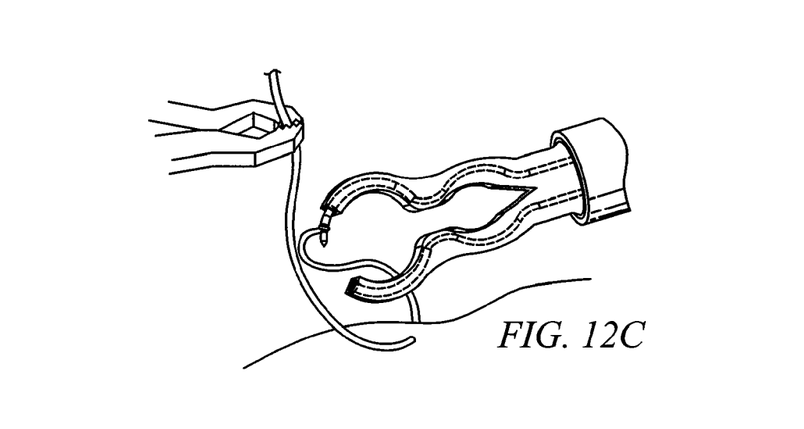
FIG. 12C is the third view thereof.
Figure 12D:
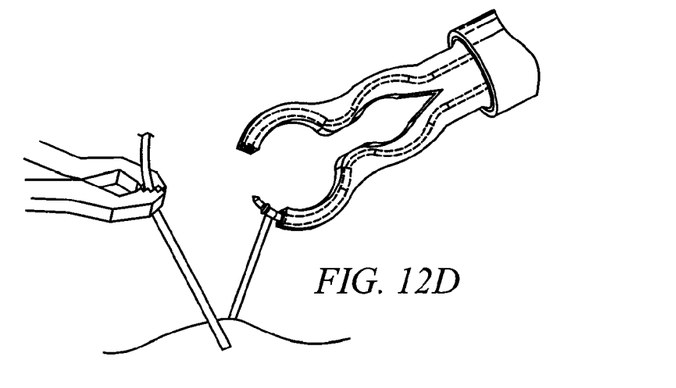
FIG. 12D is the fourth step thereof.
Figure 12E:
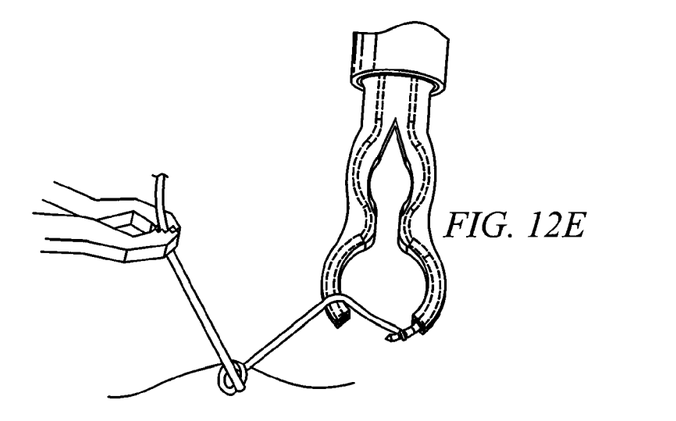
FIG. 12E is the fifth step thereof.
Figure 12F:
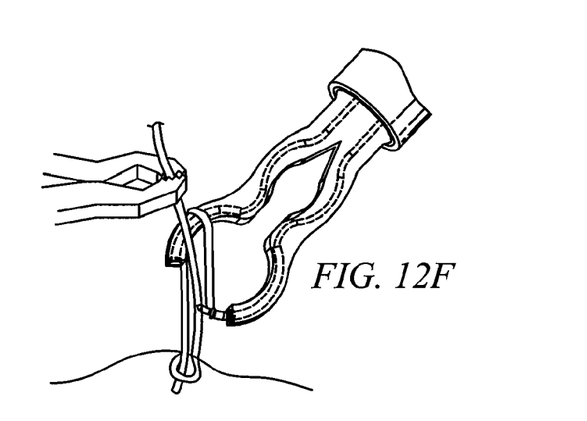
FIG. 12F is the sixth step thereof.

FIG. 7 depicts reduced diameter shaft 30 that is formed integrally with shaft 26. Key 32 is formed in reduced diameter shaft 30 near the distal end thereof. As disclosed above, rotation of toggle knob 24 effects conjoint rotation of shaft 26. More particularly, when toggle knob 24 is in a first position, key 32 is in a 12:00 position as depicted in FIGS. 7 and 11. When toggle knob 24 is in a second position, key 32 is in a 6:00 position as perhaps best understood in connection with FIG. 11.

Making reference now to FIGS. 8, 9A, 9B and 11, key 32 engages keyway 34a formed in first control plunger 36a when toggle knob 24 is in said first position and key 32 engages keyway 34b formed in plunger 36b when toggle knob 24 is rotated into its second position. Control plunger 36a is therefore extended and retracted conjointly with extension and retraction of shaft 26 when key 32 is in said first position and control plunger 36b is extended and retracted conjointly with extension and retraction of shaft 26 when key 32 is in said second position.

As perhaps best depicted in FIGS. 2-6, 9A and 11, elongate flexible wire 38a is secured at its proximal end to the distal end of first control plunger 36a and elongate flexible wire 38b is secured at its proximal end to the distal end of second control plunger 36b. The distal end of flexible wire 38a is secured to needle carrier 18 and the distal end of flexible wire 38b is secured to needle holder 20.

FIG. 11 depicts spring 14a. It is positioned between a proximal end of pusher 14 and the proximal end of shaft 26. Squeezing pusher 14 like a trigger loads spring 14a and displaces shaft 26 in a proximal to distal direction, extending shaft 26, and releasing the pressure on pusher 14 unloads spring 14a and pulls shaft 26 in a distal to proximal direction, retracting shaft 26. Accordingly, when toggle knob 24 is in its first position, such squeezing and releasing of pusher 14 operates to push and pull (extend and retract) control plunger 36a and hence needle carrier 18 by means of first flexible wire 38a. When toggle knob 24 is in its second position, such pushing and pulling of pusher 14 operates to push and pull (extend and retract) control plunger 36b and hence needle holder 20 by means of second flexible wire 38b.

Pusher 14, when squeezed, secures a suture, not depicted, to the center of needle 22. Needle 22, being pointed on both ends as at 22a, 22b, allows passage through the tissue in both directions.

The suturing and knot tying procedure is quick and simple for surgeons and safe for patients. The steps of the procedure include loading needle 22 and suture to needle holder 20, rotating sheath 28 and pushing it as indicated by directional arrow 29a, inserting tool 10 inside a patient's body, retracting sheath 26 in the direction indicated by directional arrow 29b to open arms 16a, 16b, rotating toggle knob 24 to the same side as needle 22 so that key 32 engages keyway 34a, and activating pusher 14 by pressing on it with a trigger finger, thereby loading spring 14a as aforesaid, to displace needle carrier 18 in a proximal to distal direction.

The sheath of the proposed device is 11.5 mm in diameter and can be used on a 12-mm port, but at the tip of the device, the arms are 15 mm and cannot be inserted into body by using a 12 mm port. The arms are bigger than the 12-mm port. Therefore the sheath is used to make smaller sized arms. The two arms can be closed by sliding the sheath from back to front. Once the sheath is retracted, the suturing arms return to their original positions.

Needle 22 with the suture goes through the tissue and then stays on opposite arm 16b because it is press fit into needle holder 20. Device 10 is then ready for the next maneuver.

Figure 10B:
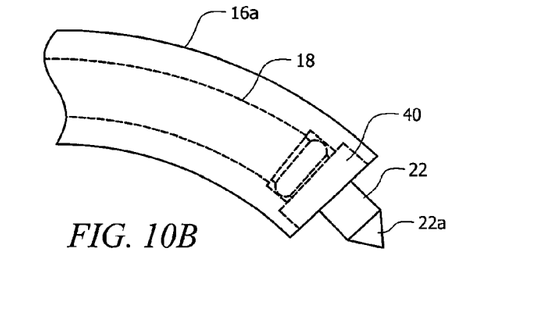
FIG. 10B is an enlarged elevational view of the needle when press fit into the lumen of a needle carrier or holder.
Figure 10C:
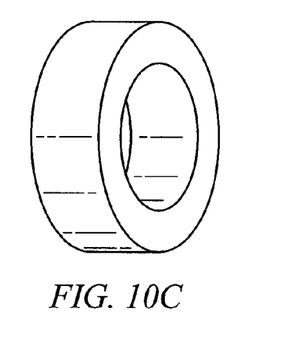
FIG. 10C is a perspective view of the sleeve that engages the needle when it is fully received within a needle carrier or holder.

FIG. 10C depicts flexible and resilient sleeve 40 that is positioned at the distal end of needle carrier 18, in the lumen thereof, as depicted in FIG. 10B, it being understood that a similar sleeve 40 is also positioned in the lumen of needle holder 20 at its distal end. The enlarged middle 22c of needle 22, depicted in FIG. 10A, enters into the lumen of sleeve 40 and is press fit thereinto as best understood in connection with FIG. 10B. The press fit is overcome so that needle 22 can extend from needle carrier 18 when pusher 14 is displaced as aforesaid until it reaches sleeve 40 in the lumen of needle holder 20 where it is maintained when needle carrier 18 is retracted. The same but reverse procedure delivers needle 22 from needle holder 20 to needle carrier 18.

Device 10 enables a surgeon to perform suturing and knot tying procedures through extra-corporeal or intra-corporeal knot tying approaches. The tool can be used to tie square knots, a surgeon's knot, and a variety of other knots. FIGS. 12A-12F provide an animation for a square knot, for example.

It will thus be seen that the objects set forth above, and those made apparent from the foregoing disclosure, are efficiently attained and since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A laparoscopic suturing device, comprising:
a handle and an elongate shaft mounted to said handle;
a toggle knob secured to said elongate shaft so that said elongate shaft is rotatable conjointly with said toggle knob when said toggle knob is rotated about a longitudinal axis of said elongate shaft;
a pair of opposed jaws that open and close relative to one another;
each of said jaws having a hollow structure;
a needle carrier slideably disposed in a lumen of a first jaw;
a needle holder slideably disposed in a lumen of a second jaw;
a truncate needle having a first pointed end and a second pointed end;
said truncate needle adapted to be press fit into a distal end of the needle carrier when the needle carrier is in a retracted position in the lumen of the first jaw with said first pointed end exposed from the needle carrier and said truncate needle adapted to be press fit into a distal end of the needle holder when the needle holder is in a retracted position in the lumen of the second jaw with said second pointed end exposed from the needle holder;
a spring-loaded pusher cooperatively positioned relative to said handle;
said spring-loaded pusher adapted to advance said distal end of said needle carrier out of the lumen in the first jaw towards the second jaw and retract said distal end of said needle carrier back into the lumen of the first jaw when said toggle knob is in a first position;
said spring-loaded pusher adapted to advance said distal end of said needle holder out of the lumen in the second jaw towards the first jaw and retract said distal end of said needle holder back into the lumen of the second jaw when said toggle knob is in a second position; and
whereby the tool assists a surgeon in suturing tissue captured between said jaws.

2. A laparoscopic suturing device, comprising:
a needle having a first end longitudinally received by a needle carrier when a second end of said needle is not longitudinally received by a needle holder, wherein longitudinally received includes a longitudinal axis of the needle aligned with a longitudinal axis of the needle carrier or the needle holder;
said needle having the second end longitudinally received by said needle holder when said first end is not longitudinally received by said needle carrier, wherein longitudinally received includes a longitudinal axis of the needle aligned with a longitudinal axis of the needle carrier or the needle holder;
said needle holder securing said needle through a press fit when said needle holder is disposed in a lumen;
said needle carrier securing said needle through a press fit when said needle carrier is disposed in a lumen;
said needle carrier and said needle holder adapted to advance out of their respective lumens towards one another; and
said first end of said needle being pointed and said second end of said needle being pointed, a first point being exposed to a suture when said needle is secured by said needle carrier and a second point being exposed to said suture when said needle is secured by said needle holder.

3. The device of claim 2, further comprising:
a sheath slideably mounted relative to a shaft;
first and second arms being forced toward one another when said sheath is displaced in a first direction;
said first and second arms formed of a flexible and resilient material and returning under an inherent bias to a position of repose when said shaft is displaced in a second direction that is opposite to said first direction.

4. The device of claim 3, further comprising:
said shaft having a reduced diameter extent formed integrally therewith;
a key formed in said reduced diameter shaft near a distal end thereof;
said key being in a 12:00 position, with respect to a longitudinal axis of said shaft, when a toggle knob is in a first position;
said key being in a 6:00 position, with respect to a longitudinal axis of said shaft, when a toggle knob is in a second position;
a first control plunger having a keyway formed therein;

a second control plunger having a keyway formed therein;

said key engaging the keyway formed in said first control plunger when said toggle knob is in said first position and said key engaging the keyway formed in said second control plunger when said toggle knob is rotated into said second position;

said first control plunger being extended and refracted conjointly with extension and retraction of said shaft when said key is in said first position and said second control plunger being extended and retracted conjointly with extension and retraction of said shaft when said key is in said second position.

5. The device of claim 4, further comprising:

a first elongate flexible wire secured at a proximal end thereof to a distal end of said first control plunger;

a second elongate flexible wire secured at a proximal end thereof to a distal end of said second control plunger;

a distal end of said first flexible wire being secured to said needle carrier; and a distal end of said second flexible wire being secured to said needle holder.

6. The device of claim 5, further comprising:

a spring positioned between an internal end of a pusher and a proximal end of said shaft;

said spring, when compressed, pushing said shaft in a proximal to distal direction, extending said shaft;

said spring, when decompressed, pulling said shaft in a distal to proximal direction, retracting said shaft;

said pushing and pulling of said shaft, when said toggle knob is in said first position, respectively extending and retracting said first control plunger and hence said needle carrier by means of said first elongate flexible wire; and said pushing and pulling of said shaft, when said toggle knob is in said second position, respectively extending and retracting said second control plunger and hence said needle holder by means of said second elongate flexible wire.

7. The device of claim 6, further comprising:

a first flexible and resilient sleeve positioned in a lumen of said needle carrier at the distal end of said needle carrier;

a second flexible and resilient sleeve positioned in a lumen of said needle holder at the distal end of said needle holder;

said needle being enlarged mid-length thereof;

said enlarged middle being press fit into the lumen of said sleeve;

said press fit being overcome so that said needle can extend from said needle carrier when said pusher is displaced until said needle reaches the sleeve positioned in the lumen of said needle holder where it is maintained when said needle carrier is retracted; and said needle being delivered from said needle holder to said needle carrier when said press fit is overcome so that said needle can extend from said needle holder when said pusher is displaced until said needle reaches the sleeve positioned in the lumen of said needle carrier where it is maintained when said needle holder is retracted.

* * * * *